United States Patent
Hladio et al.

(10) Patent No.: US 9,314,188 B2
(45) Date of Patent: Apr. 19, 2016

(54) COMPUTER-ASSISTED JOINT REPLACEMENT SURGERY AND NAVIGATION SYSTEMS

(75) Inventors: Andre Novomir Hladio, Ottawa (CA); Richard Tyler Fanson, Stoney Creek (CA); Armen Garo Bakirtzian, Kitchener (CA)

(73) Assignee: INTELLIJOINT SURGICAL INC., Waterloo (CA)

( * ) Notice: Subject to any disclaimer, the term of this patent is extended or adjusted under 35 U.S.C. 154(b) by 466 days.

(21) Appl. No.: 13/445,777

(22) Filed: Apr. 12, 2012

(65) Prior Publication Data

US 2013/0274633 A1    Oct. 17, 2013

(51) Int. Cl.
*A61B 5/107*    (2006.01)
*A61B 5/00*    (2006.01)

(52) U.S. Cl.
CPC ............ *A61B 5/1072* (2013.01); *A61B 5/4887* (2013.01)

(58) Field of Classification Search
CPC ..... A61B 5/1114; A61B 19/5244; A61B 5/72
USPC .......................................................... 600/587
See application file for complete search history.

(56) References Cited

U.S. PATENT DOCUMENTS

| | | |
|---|---|---|
| 4,994,064 A | 2/1991 | Aboczky |
| 5,122,145 A | 6/1992 | Fishbane |
| 5,141,512 A | 8/1992 | Farmer et al. |
| 5,227,985 A | 7/1993 | DeMenthon |
| 5,249,581 A | 10/1993 | Horbal et al. |
| 5,480,439 A | 1/1996 | Bisek et al. |
| 5,611,353 A | 3/1997 | Dance et al. |
| 5,700,268 A | 12/1997 | Bertin |
| 5,772,610 A | 6/1998 | McGorry et al. |
| 5,807,252 A | 9/1998 | Hassfeld et al. |
| 5,854,843 A | 12/1998 | Jacknin et al. |

(Continued)

FOREIGN PATENT DOCUMENTS

| | | |
|---|---|---|
| EP | 1563810 B1 | 3/2010 |
| FR | 2684287 A1 | 4/1993 |

(Continued)

OTHER PUBLICATIONS

L.B. Solomon, et al., "Surgical Anatomy for Pelvic External Fixation", p. 674-682, Clinical Anatomy, 2008, Wiley-Liss, Inc.

(Continued)

*Primary Examiner* — Jeffrey G Hoekstra
*Assistant Examiner* — Patrick Fernandes
(74) *Attorney, Agent, or Firm* — Gowling WLG (Canada) LLP

(57) ABSTRACT

The present invention generally relates to computer-assisted joint replacement surgery, and corresponding navigation systems. The systems and methods presented find particular use in performing hip replacement surgery. For example, in one embodiment, there is provided a system and method for: (a) measuring a pre-dislocation positional relationship between a patient's pelvis and the patient's femur; (b) performing a post-dislocation femoral registration of the femur; (c) tracking the position of the femur relative to the pelvis during a reduction procedure; (d) calculating a change in leg length and a change in offset, after the reduction procedure, based on the femoral registration and the pre-dislocation positional relationship between the pelvis and the femur; and (e) conveying the change in leg length and the change in offset.

18 Claims, 10 Drawing Sheets

(56) References Cited

U.S. PATENT DOCUMENTS

| | | |
|---|---|---|
| 5,880,976 A | 3/1999 | DiGioia III et al. |
| 5,956,660 A | 9/1999 | Neumann |
| 5,966,827 A | 10/1999 | Horvath et al. |
| 6,009,189 A | 12/1999 | Schaack |
| 6,061,644 A | 5/2000 | Leis |
| 6,161,032 A | 12/2000 | Acker |
| 6,395,005 B1 | 5/2002 | Lovell |
| 6,450,978 B1 | 9/2002 | Brosseau et al. |
| 6,529,765 B1 | 3/2003 | Franck et al. |
| 6,607,487 B2 | 8/2003 | Chang et al. |
| 6,711,431 B2* | 3/2004 | Pratt et al. ............... 600/426 |
| 6,718,194 B2* | 4/2004 | Kienzle, III ............... 600/424 |
| 6,917,827 B2 | 7/2005 | Kienzle, III |
| 6,925,339 B2 | 8/2005 | Grimm et al. |
| 6,978,167 B2 | 12/2005 | Dekel et al. |
| 6,988,009 B2 | 1/2006 | Grimm et al. |
| 7,001,346 B2 | 2/2006 | White |
| 7,130,676 B2 | 10/2006 | Barrick |
| 7,302,355 B2 | 11/2007 | Jansen et al. |
| 7,314,048 B2 | 1/2008 | Couture et al. |
| 7,392,076 B2 | 6/2008 | Moctezuma de La Barrera |
| 7,400,246 B2 | 7/2008 | Breeding |
| 7,407,054 B2 | 8/2008 | Seiler et al. |
| 7,412,777 B2 | 8/2008 | Pelletier et al. |
| 7,419,492 B2 | 9/2008 | Yoon et al. |
| 7,427,272 B2 | 9/2008 | Richard et al. |
| 7,431,736 B2 | 10/2008 | Maroney et al. |
| 7,559,931 B2 | 7/2009 | Stone |
| 7,588,571 B2 | 9/2009 | Olsen |
| 7,594,933 B2 | 9/2009 | Kammerzell et al. |
| 7,634,306 B2 | 12/2009 | Sarin et al. |
| 7,657,298 B2 | 2/2010 | Moctezuma de La Barrera et al. |
| 7,668,584 B2 | 2/2010 | Jansen |
| 7,749,223 B2* | 7/2010 | Lavigna et al. ............... 606/53 |
| 7,753,921 B2 | 7/2010 | Leitner |
| 7,769,429 B2 | 8/2010 | Hu |
| 7,780,681 B2* | 8/2010 | Sarin et al. ............... 606/130 |
| 7,840,256 B2 | 11/2010 | Lakin et al. |
| 7,876,942 B2 | 1/2011 | Gilboa |
| 7,877,131 B2 | 1/2011 | Jansen et al. |
| 7,885,705 B2* | 2/2011 | Murphy ............... 600/426 |
| 7,927,338 B2 | 4/2011 | Laffargue et al. |
| 7,970,190 B2 | 6/2011 | Steinle et al. |
| 7,995,280 B2 | 8/2011 | Kuss et al. |
| 8,000,926 B2 | 8/2011 | Roche et al. |
| 8,007,448 B2 | 8/2011 | Moctezuma de La Barrera |
| 8,034,057 B2 | 10/2011 | Penenberg |
| 8,057,482 B2 | 11/2011 | Stone et al. |
| 8,152,726 B2 | 4/2012 | Amiot et al. |
| 8,165,659 B2 | 4/2012 | Sheffer et al. |
| 8,167,823 B2 | 5/2012 | Nyez et al. |
| 8,177,850 B2 | 5/2012 | Rudan et al. |
| 8,202,324 B2 | 6/2012 | Meulink et al. |
| 8,206,405 B2 | 6/2012 | Beverland et al. |
| 8,308,663 B2 | 11/2012 | Tuma et al. |
| 8,337,426 B2 | 12/2012 | Nyez |
| 8,400,312 B2 | 3/2013 | Hotokebuchi et al. |
| 8,425,557 B2 | 4/2013 | Kuiper et al. |
| 8,467,851 B2 | 6/2013 | Mire et al. |
| 8,482,606 B2 | 7/2013 | Razzaque et al. |
| 8,554,307 B2 | 10/2013 | Razzaque et al. |
| 8,585,598 B2 | 11/2013 | Razzaque et al. |
| 8,641,621 B2 | 2/2014 | Razzaque et al. |
| 8,657,809 B2 | 2/2014 | Schoepp |
| 8,670,816 B2 | 3/2014 | Green et al. |
| 8,690,776 B2 | 4/2014 | Razzaque et al. |
| 2002/0077540 A1 | 6/2002 | Kienzle, III |
| 2002/0087101 A1 | 7/2002 | Barrick et al. |
| 2002/0198451 A1 | 12/2002 | Carson |
| 2003/0069591 A1 | 4/2003 | Carson et al. |
| 2003/0105470 A1 | 6/2003 | White |
| 2003/0153978 A1 | 8/2003 | Whiteside |
| 2003/0163142 A1 | 8/2003 | Paltieli et al. |
| 2003/0208296 A1 | 11/2003 | Brisson et al. |
| 2004/0102792 A1 | 5/2004 | Sarin et al. |
| 2004/0106861 A1 | 6/2004 | Leitner |
| 2004/0143340 A1 | 7/2004 | Tuma et al. |
| 2004/0147926 A1 | 7/2004 | Iversen |
| 2004/0230199 A1* | 11/2004 | Jansen et al. ............... 606/91 |
| 2004/0243148 A1 | 12/2004 | Wasielewski |
| 2004/0254586 A1 | 12/2004 | Sarin et al. |
| 2005/0015002 A1 | 1/2005 | Dixon et al. |
| 2005/0021044 A1 | 1/2005 | Stone et al. |
| 2005/0049524 A1 | 3/2005 | Lefevre et al. |
| 2005/0065617 A1 | 3/2005 | Moctezuma de la Barrera et al. |
| 2005/0149050 A1 | 7/2005 | Stifter et al. |
| 2005/0245820 A1 | 11/2005 | Sarin |
| 2005/0251026 A1 | 11/2005 | Stone |
| 2005/0288609 A1 | 12/2005 | Warner et al. |
| 2006/0004284 A1 | 1/2006 | Grunschlager et al. |
| 2006/0084889 A1 | 4/2006 | Drumm et al. |
| 2006/0089657 A1 | 4/2006 | Broers et al. |
| 2006/0095047 A1 | 5/2006 | De La Barrera |
| 2006/0155382 A1 | 7/2006 | Katzman |
| 2006/0161052 A1 | 7/2006 | Colombet et al. |
| 2006/0189864 A1 | 8/2006 | Paradis et al. |
| 2006/0190011 A1 | 8/2006 | Ries |
| 2006/0293614 A1 | 12/2006 | Radinsky et al. |
| 2007/0118139 A1 | 5/2007 | Cuellar et al. |
| 2007/0179568 A1 | 8/2007 | Nycz et al. |
| 2007/0209220 A1* | 9/2007 | Murphy ............... 33/512 |
| 2007/0225731 A1 | 9/2007 | Couture et al. |
| 2007/0239281 A1 | 10/2007 | Gotte et al. |
| 2007/0249967 A1 | 10/2007 | Buly et al. |
| 2007/0270686 A1 | 11/2007 | Ritter et al. |
| 2008/0027312 A1 | 1/2008 | Dick |
| 2008/0033442 A1 | 2/2008 | Amiot et al. |
| 2008/0051910 A1 | 2/2008 | Kammerzell et al. |
| 2008/0077004 A1 | 3/2008 | Henning |
| 2008/0125785 A1 | 5/2008 | Chana |
| 2008/0132783 A1 | 6/2008 | Revie et al. |
| 2008/0146969 A1* | 6/2008 | Kurtz ............... 600/595 |
| 2008/0172055 A1 | 7/2008 | Mollard et al. |
| 2008/0183104 A1 | 7/2008 | Tuma et al. |
| 2008/0195109 A1 | 8/2008 | Hunter et al. |
| 2008/0214960 A1 | 9/2008 | Hodgson et al. |
| 2008/0228188 A1 | 9/2008 | Birkbeck et al. |
| 2008/0249394 A1 | 10/2008 | Giori et al. |
| 2008/0255584 A1 | 10/2008 | Beverland et al. |
| 2008/0269596 A1 | 10/2008 | Revie et al. |
| 2008/0294265 A1 | 11/2008 | Warkentine et al. |
| 2008/0312529 A1 | 12/2008 | Amiot et al. |
| 2008/0319313 A1 | 12/2008 | Boivin et al. |
| 2009/0087050 A1 | 4/2009 | Gandyra |
| 2009/0099570 A1 | 4/2009 | Paradis et al. |
| 2009/0105714 A1 | 4/2009 | Kozak |
| 2009/0125117 A1* | 5/2009 | Paradis et al. ............... 623/22.11 |
| 2009/0143670 A1 | 6/2009 | Daigneault et al. |
| 2009/0163930 A1 | 6/2009 | Aoude et al. |
| 2009/0171370 A1 | 7/2009 | Yoon et al. |
| 2009/0209343 A1 | 8/2009 | Foxlin et al. |
| 2009/0248044 A1 | 10/2009 | Amiot et al. |
| 2009/0281545 A1 | 11/2009 | Stubbs |
| 2009/0289806 A1 | 11/2009 | Thornberry |
| 2009/0314925 A1 | 12/2009 | Van Vorhis et al. |
| 2009/0316967 A1 | 12/2009 | Dardenne et al. |
| 2009/0318931 A1 | 12/2009 | Stone et al. |
| 2010/0016705 A1 | 1/2010 | Stone |
| 2010/0063509 A1 | 3/2010 | Borja et al. |
| 2010/0069911 A1 | 3/2010 | Borja et al. |
| 2010/0076505 A1 | 3/2010 | Borja |
| 2010/0100081 A1* | 4/2010 | Roche ............... 600/587 |
| 2010/0137869 A1 | 6/2010 | Borja et al. |
| 2010/0137871 A1 | 6/2010 | Borja |
| 2010/0153081 A1 | 6/2010 | Bellettre et al. |
| 2010/0192961 A1 | 8/2010 | Amiot et al. |
| 2010/0261998 A1* | 10/2010 | Stiehl ............... 600/424 |
| 2010/0268067 A1 | 10/2010 | Razzaque et al. |
| 2010/0299101 A1 | 11/2010 | Shimada et al. |
| 2010/0312247 A1 | 12/2010 | Tuma |
| 2011/0092858 A1 | 4/2011 | Burger et al. |
| 2011/0160572 A1 | 6/2011 | McIntosh et al. |
| 2011/0213379 A1 | 9/2011 | Blau et al. |
| 2011/0257653 A1 | 10/2011 | Hughes et al. |

(56) References Cited

U.S. PATENT DOCUMENTS

| 2011/0264009 | A1 | 10/2011 | Walter et al. |
|---|---|---|---|
| 2012/0022406 | A1 | 1/2012 | Hladio et al. |
| 2012/0029389 | A1 | 2/2012 | Amiot et al. |
| 2012/0053594 | A1 | 3/2012 | Pelletier et al. |
| 2012/0065926 | A1 | 3/2012 | Lee et al. |
| 2012/0143084 | A1 | 6/2012 | Shoham |
| 2012/0157887 | A1 | 6/2012 | Fanson et al. |
| 2012/0209117 | A1 | 8/2012 | Mozes et al. |
| 2012/0232802 | A1 | 9/2012 | Haimerl et al. |
| 2012/0283599 | A1 | 11/2012 | Borja |
| 2012/0323247 | A1 | 12/2012 | Bettenga |

FOREIGN PATENT DOCUMENTS

| WO | 2006109983 | A1 | 10/2006 |
|---|---|---|---|
| WO | 2006128301 | A1 | 12/2006 |
| WO | 2007084893 | A2 | 7/2007 |
| WO | 2007095248 | A2 | 10/2007 |
| WO | 2008151446 | A1 | 12/2008 |
| WO | 2009062314 | A1 | 5/2009 |
| WO | 2009117833 | A1 | 10/2009 |
| WO | 2010030809 | A1 | 3/2010 |
| WO | 2010063117 | A1 | 6/2010 |
| WO | 2012080840 | A1 | 6/2012 |
| WO | 2013/152436 | | 10/2013 |

OTHER PUBLICATIONS

Seidel, Geoffrey K., et al., "Hip Joint Center Location from Palpable Bony Landmarks—A Cadaver Study", J. Biomechanics, vol. 28, No. 8, pp. 995-998, 1995.

Written Opinion of the International Search Authority dated Feb. 18, 2010, relating to PCT International Patent Application No. PCT/CA2009/001765 issued from the Canadian Intellectual Property Office.

International Preliminary Report on Patentability dated Jun. 7, 2011, relating to PCT International Patent Application No. PCT/CA2009/001765 issued from the International Bureau of WIPO.

Nogler, Michael, et al., "Reduced variability in cup positioning: the direct anteror surgical approach using navigation", Nov. 6, 2009, Informa Healthcare, Acta Orthapaedica, 79:6, 789-793.

Toshiya Kanoh, MD, et al., "Accurate Acetabular Component Orientation After Total Hip Arthroplasty Using an Acetabular Alignment Guide", The Journal of Arthroplasty, vol. 25, No. 1, 2010, p. 81-85.

DiGioia, Anthony M., et al., "Comparison of a Mechanical Acetabular Alignment Guide with Computer Placement of the Socket", The Journal of Arthroplasty, vol. 17, No. 3, 2002, p. 359-360.

DiGioia, Anthony M., et al., "Surgical Navigation for Total Hip Replacement with the Use of Hipnav", Operative Techniques in Orthopaedics, vol. 10, No. 1, Jan. 2000, p. 3-8.

International Search Report and Written Opinion dated May 22, 2012, relating to PCT International Patent Application No. PCT/IB2011/003246 issued from the Canadian Intellectual Property Office.

Birrell et al., "Projecting the need for hip replacement over the next three decades: influence of changing demography and threshold for surgery", Annals of the Rheumatic Diseases, vol. 58, p. 569-72, 1999.

Written Opinion dated Jul. 22, 2013 issued from the Canadian Intellectual Property Office relating to PCT International Application No. PCT/CA2013/000351.

International Search Report issued from the Canadian Intellectual Property Office relating to PCT International Application No. PCT/CA2009/001765.

Kanoh et al, "Accurate Acetabular Component Orientation After Total Hip Arthroplasty Using an Acetabular Alignment Guide," The Journal of Arthroplasty, vol. 25, No. 1, pp. 1-6 (2010).

International Search Report issued from the Canadian Intellectual Property Office relating to PCT International Application No. PCT/CA2013/000351.

* cited by examiner

COMPUTER-ASSISTED JOINT REPLACEMENT SURGERY AND NAVIGATION SYSTEMS

SUMMARY

The present invention generally relates to computer-assisted joint replacement surgery, and corresponding navigation systems. The systems and methods presented find particular use in performing hip replacement surgery.

For example, in one embodiment, there is provided a system and method for: (a) measuring a pre-dislocation positional relationship between a patient's pelvis and the patient's femur; (b) performing a post-dislocation femoral registration of the femur; (c) tracking the position of the femur relative to the pelvis during a reduction procedure; (d) calculating a change in leg length and a change in offset, after the reduction procedure, based on the femoral registration and the pre-dislocation positional relationship between the pelvis and the femur; and (e) conveying the change in leg length and the change in offset.

Example embodiments generally include placing a sensor unit on the pelvis, and a sensor unit on the femur. The sensor units are used to measure a pre-dislocation positional relationship between the pelvis and the femur in six degrees-of-freedom (DOF). For example, the sensor units may be used to measure 3-DOF of position and 3-DOF of orientation. During a reduction procedure, the sensor units are used to track and compare the positional relationship between the pelvis and the femur, before and after surgery. Any post-reduction change in positional relationship can be conveyed as changes in leg length and offset. To do so, the femoral coordinate system is registered, prior to reduction, but post-dislocation. Femoral registration is typically performed by coupling a sensor unit to a registration tool (e.g., a surgical broach), and coupling the registration tool to the femur (e.g., inserting the broach into the femur). When the registration tool is coupled to the femur, a measurement between the sensor unit on the registration tool and the sensor unit on the femur can "teach" the system the femoral coordinate system, which in turn teaches the system the directions of leg length and offset.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use the claimed systems and methods.

INCORPORATION BY REFERENCE

Figure 1:
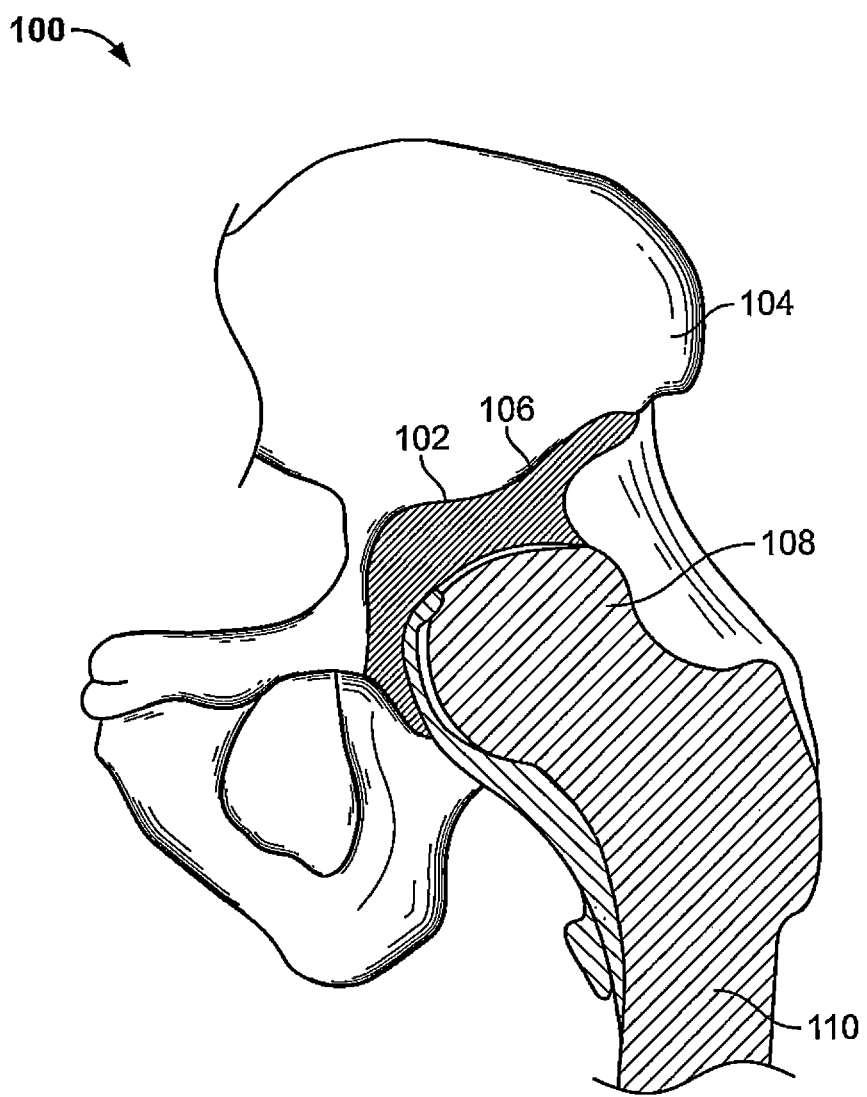
FIG. 1 is a sectional view of a native hip joint.

Except for any term definitions that conflict with the term definitions provided herein, the related, co-owned, and co-pending U.S. patent application Ser. No. 13/328,997 is incorporated herein by reference, in its entirety.

DEFINITIONS

Prior to describing the present invention in detail, it is useful to provide definitions for key terms and concepts used herein. Unless defined otherwise, all technical and scientific terms used herein have the same meaning as commonly understood by one of ordinary skill in the art to which this invention belongs.

Matching Coordinate System: As used herein, the term "matching coordinate system" is intended to generally include coordinate systems having parallel or collinear positional axes. For example, the coordinate systems of the broach "matches" the coordinate system of the femur if the broach is aligned and positioned such that the positional axes of the broach are collinear or parallel to the positional axes of the femur.

"Positional Relationship" or "Relative Position": The terms "positional relationship" or "relative position" generally refer to a rigid-body transformation between coordinate systems. In Cartesian space, the rigid-body transformation consists of six degrees-of-freedom (DOF): 3-DOF for translational position and 3-DOF for rotational (or orientation) position. In general, the terms "positional relationship" or "relative position" encompass one through six DOF. The number of DOF of a positional relationship may be explicitly stated (e.g., 2-DOF), or implied by the context (e.g., 3-DOF are generally used to describe orientation). For example, in some instances, positional relationship is determined by first determining the 6-DOF positioning, then extracting the desired positional information described by less than 6-DOF.

"Register" or "Registration": The terms "register" or "registration" generally refer to the act of determining a relative position between an object (e.g., pelvis, femur, instrument) and a respective sensor unit.

Sensor Unit: As used herein, a sensor unit is broadly defined as any system component that includes at least a receiver or reader unit and/or a beacon or emitter unit. For example, an optical reader is an example of a "sensor unit." Similarly, a beacon or emitter, which is capable of being sensed by an optical reader, is another example of a "sensor unit." Other examples of sensor units are presented in co-pending U.S. patent application Ser. No. 13/328,997, which has been incorporated by reference herein.

Before the present invention is described in greater detail, it is to be understood that this invention is not limited to particular embodiments described, and as such may vary. It is also to be understood that the terminology used herein is for the purpose of describing particular embodiments only, and is not intended to be limiting. The scope of the present invention will be limited only by the appended claims.

DETAILED DESCRIPTION

Joint replacement surgery involves replacing an existing joint with artificial prosthetic components. Examples of common joint replacements include hip replacements and knee replacements. Hip replacement may be segmented into three types: primary, revision, and resurfacing. Primary hip replacement, also called Total Hip Arthroplasty (THA), involves the surgical excision of the head and proximal neck of the femur, and the removal of the acetabular cartilage and subchondral bone. Commonly, an artificial canal is created in the proximal medullary region of the femur, and a metal femoral prosthesis is inserted into the femoral medullary canal. An acetabular component or implant is then inserted in the enlarged acetabular space. Hip resurfacing, like THA, involves the surgical removal of the acetabular cartilage and subchondral bone, and the subsequent insertion of an acetabular prosthetic. Unlike THA, resurfacing does not involve the excision of the femoral head, but rather covering the existing femoral head with a prosthetic cap, which mates with the acetabular prosthetic. Revision hip surgery is typically performed when an artificial hip joint fails. Revision hip surgery typically involves the replacement of one or more of the failed artificial prosthetic components.

For ease of explanation, the systems and methods described herein are described with reference to performing a THA procedure. However, it will be evident to a person of skill in the art that the systems and methods presented may be applied to other types of hip replacement (e.g., hip resurfacing, revision hip replacement, etc.), as well as to other surgical procedures where a prosthesis is implanted (e.g., knee replacement surgery). Before presenting a detailed description of the embodiments of the present invention, a brief description of a THA procedure will be provided with reference to FIGS. 1-3.

Figure 2:
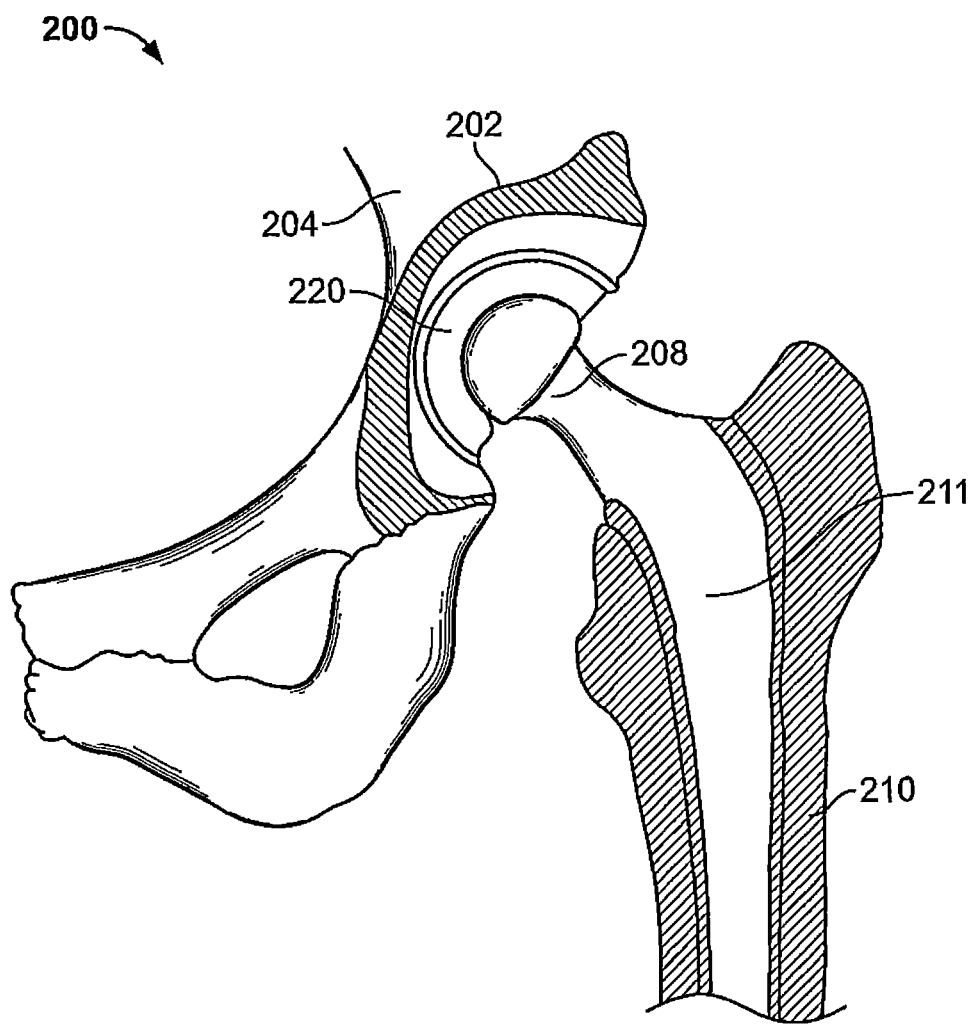
FIG. 2 is a sectional view of a hip joint after Total Hip Arthroplasty.

FIG. 1 is a sectional view of a native hip joint 100. As shown in FIG. 1, the hip joint 100 includes an acetabulum 102 (or socket) in the pelvic bone 104, which is lined with acetabular cartilage 106. The femoral head 108, at the upper end of the femur 110, is received in the acetabulum 102. FIG. 2 is a sectional view of a hip joint 200 after THA. During THA, the femur 210 is first dislocated from the hip joint 200. The acetabulum 202 is then reamed out, and an acetabular component or implant 220 is attached to the acetabulum 202. The femoral head of the femur 210 is also removed. The femur 210 is opened out, and a stem component 211, referred to as the femoral component or femoral implant, is inserted into a canal created within the femur 210. A ball component 208 is then attached to the stem component 211, to mate with the acetabular implant 220. A reduction procedure is then performed to return the femur 210 to its proper position, with the ball component 208 set within the acetabular implant 220.

Figure 3B:
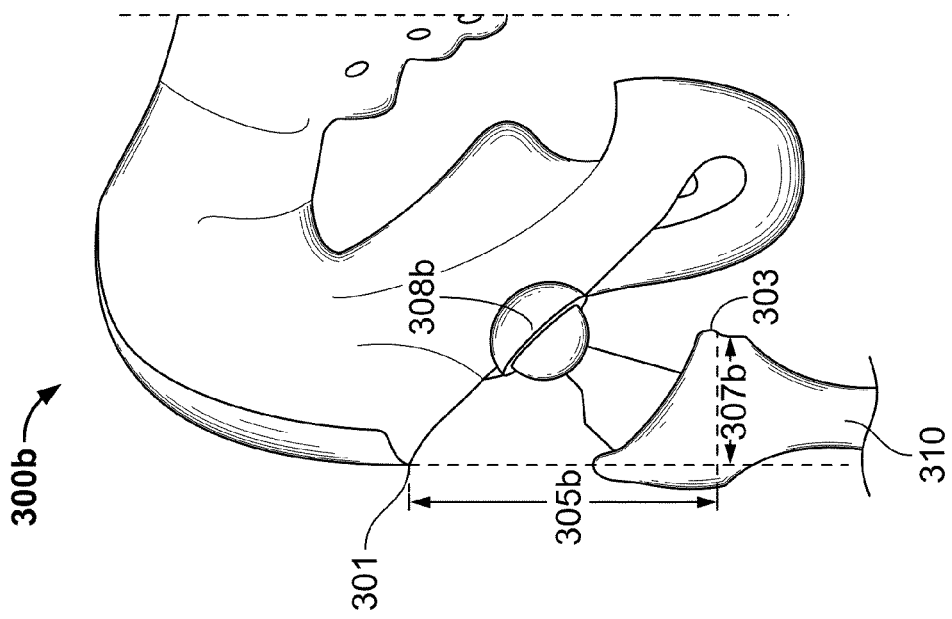
FIGS. 3A and 3B are comparative diagrams of a hip joint, illustrating the measures of leg length and offset, before and after a hip replacement procedure, respectively.
Figure 3A:
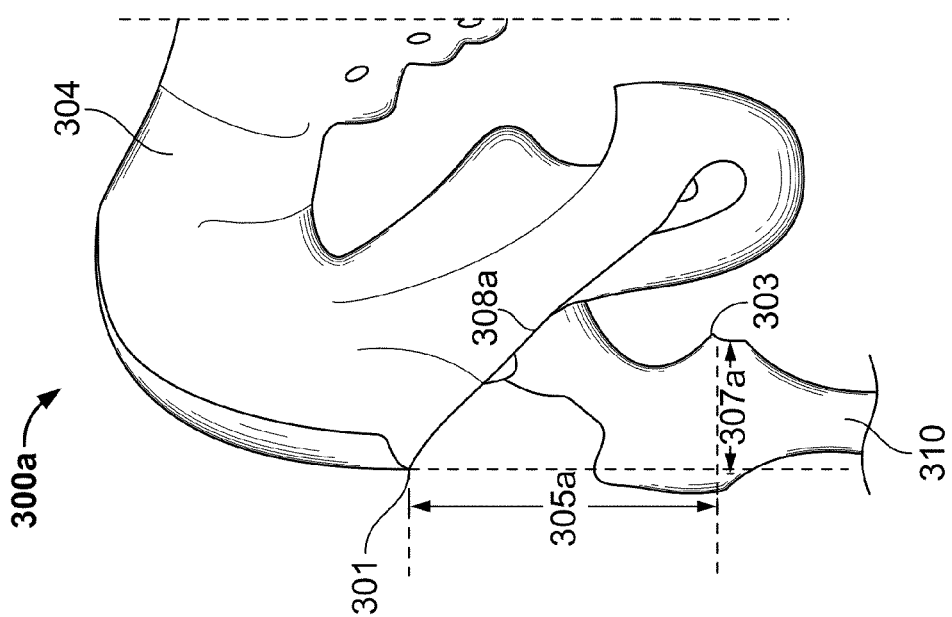

An important aspect of hip replacement is ensuring an acceptable post-reduction leg length and offset. Typically, the goal is to leave the leg length and offset unchanged as a result of the procedure. However, surgeons will often incorporate a small change in leg length as a corrective measure. Therefore, surgeons benefit from a precise understanding of pre- and post-dislocation leg length and offset (as well as anterior-posterior position and center of rotation of the femur). While the definitions of leg length and offset are well-documented in the literature and known to those skilled in the art, FIGS. 3A and 3B are provided to illustrate pre-dislocation and post-reduction leg length and offset. More specifically, FIGS. 3A and 3B illustrate a hip joint 300a before THA (FIG. 3A) and a hip joint 300b after THA (FIG. 3B). The original (i.e., pre-dislocation) leg length 305a and offset 307a are components of the vector between a landmark (or reference location) 301 on the pelvis 304 and a landmark 303 on the femur 310. The resulting leg length 305b and offset 307b are components of the vector between the same landmarks (i.e., landmark 301 on the pelvis 304, and landmark 303 on the femur 310).

The original leg length 305a and offset 307a may be measured using a pre-operative scan (e.g., X-ray, CT scan, and MRI), as well as the original femoral center of rotation (COR) 308a. A desired change in leg length and offset may be calculated based on a desired resulting leg length 305b and offset 307b, the original leg length 305a and offset 307a, the resulting COR 308b, as well as the dimensions of the femoral implant. However, pre- and post-operative scans, as well as other known mechanical instrumentation, may be cumbersome and ineffective for determining leg length and offset intra-operatively. As such, the systems and methods presented below aid a surgeon in achieving a desired resulting leg length and offset by monitoring the leg length and offset during surgery, using sensor units attached to the pelvis and femur, and conveying a change in leg length and offset in a meaningful way. The systems and methods presented may also be used to determine and convey the pre- and post-operative femoral COR position, including the anterior-posterior change of the femoral COR position.

For example, in one embodiment, there is provided a system and method for: (a) measuring a pre-dislocation positional relationship between a patient's pelvis and the patient's femur; (b) performing a post-dislocation femoral registration of the femur; (c) tracking the position of the femur relative to the pelvis during a reduction procedure; (d) calculating a change in leg length and a change in offset, after the reduction procedure, based on the femoral registration and the pre-dislocation positional relationship between the pelvis and the femur; and (e) conveying the change in leg length and the change in offset. Example embodiments generally include placing a sensor unit on the pelvis, and a sensor unit on the femur. The sensor units are used to measure a pre-dislocation positional relationship between the pelvis and the femur in six degrees-of-freedom (DOF). In other words, positional relationship implies determining the positioning between two rigid bodies and their corresponding coordinate systems, neither of the rigid bodies being considered fixed to a global coordinate system. For example, the sensor units may be used to measure 3-DOF of position and 3-DOF of orientation. During a reduction procedure, the sensor units are used to track and compare the positional relationship between the pelvis and the femur, before and after surgery. Any post-reduction change in positional relationship can be conveyed as changes in leg length and offset. To do so, the femoral coordinate system is registered, prior to reduction, but post-dislocation. Femoral registration is typically performed by coupling a sensor unit to a registration tool (e.g., a surgical broach), and coupling the registration tool to the femur (e.g., inserting the broach into the femur). When the registration tool is coupled to the femur, a measurement between the sensor unit on the registration tool and the sensor unit on the femur can "teach" the system the femoral coordinate system, which in turn teaches the system the directions of leg length and offset.

Of note, the systems and methods presented herein are distinctly different from traditional computer-assisted surgical systems that require: 1) registrations of multiple anatomical structures (e.g., pelvic registration and femoral registration); 2) markers positioned on respective anatomical structures; and 3) fixed stereoscopic camera units stationed within the operating room to monitor the movements of the markers throughout the surgery. Because the systems and methods presented measure positional relationships between sensor units mounted directly to the anatomical structures, and perform a femoral registration to identify the relative position between a femur sensor and the femur, accurate and real-time calculations can be performed without the use of pelvic registrations and/or fixed capital equipment stationed within the operating room.

As known to those skilled in the art, pelvic registration is one of the biggest barriers to adoption of traditional navigation systems for hip arthroplasty. Pelvic registration is typically time consuming and/or inaccurate. The systems and methods presented herein, however, employ a femoral registration, and associated femoral registration tool (e.g., broach and broach sensor), to overcome the disadvantages of traditional navigation systems that require pelvic registration and/or stereoscopic camera units. For instance, femoral registration with a femoral registration tool only requires one registration measurement, instead of the at least three registration measurements required in a pelvic registration. Femoral registration can also be performed with existing surgical tools (e.g., broach), which are designed to mate with, and match orientations with, the femur. In contrast, pelvic registration requires a "mapping" of the pelvis with a stylus/pointer tool. As a result, femoral registration is more accurate because the femoral registration tool (e.g., broach) matches the anatomy of the femur and the final implant position; whereas the plane of the pelvis (e.g., anterior pelvic plane) is an arbitrary reference plane subject to inaccuracies in mapping to actual patient anatomy. Further, femoral registration using existing surgical tools (e.g., broach), allow the systems and methods presented to provide the surgeon with data that directly correlates with the trial and/or implant components that are being used in the procedure. As such, femoral registration is faster and more accurate, and more likely to receive industry adoption.

As such, the systems and methods presented can be used to significantly reduce the complexities and capital expenditures of hip replacement surgeries (as well as other joint replacement surgeries). Further, the systems and methods presented may be used in a novel computer navigation system for performing joint replacement surgery. Such a navigation system, employing sensor units mounted directly onto anatomical structures, negates the need for fixed capital equipment stationed within the operating room. Such a navigation system also overcomes many of the drawbacks of traditional navigation systems. For example, such a navigation system does not require the large capital expenses of traditional navigation systems; avoids line-of-sight complications; and typically tracks only one object at a time, thus reducing computational complexity and facilitating greater robustness.

Figure 4:
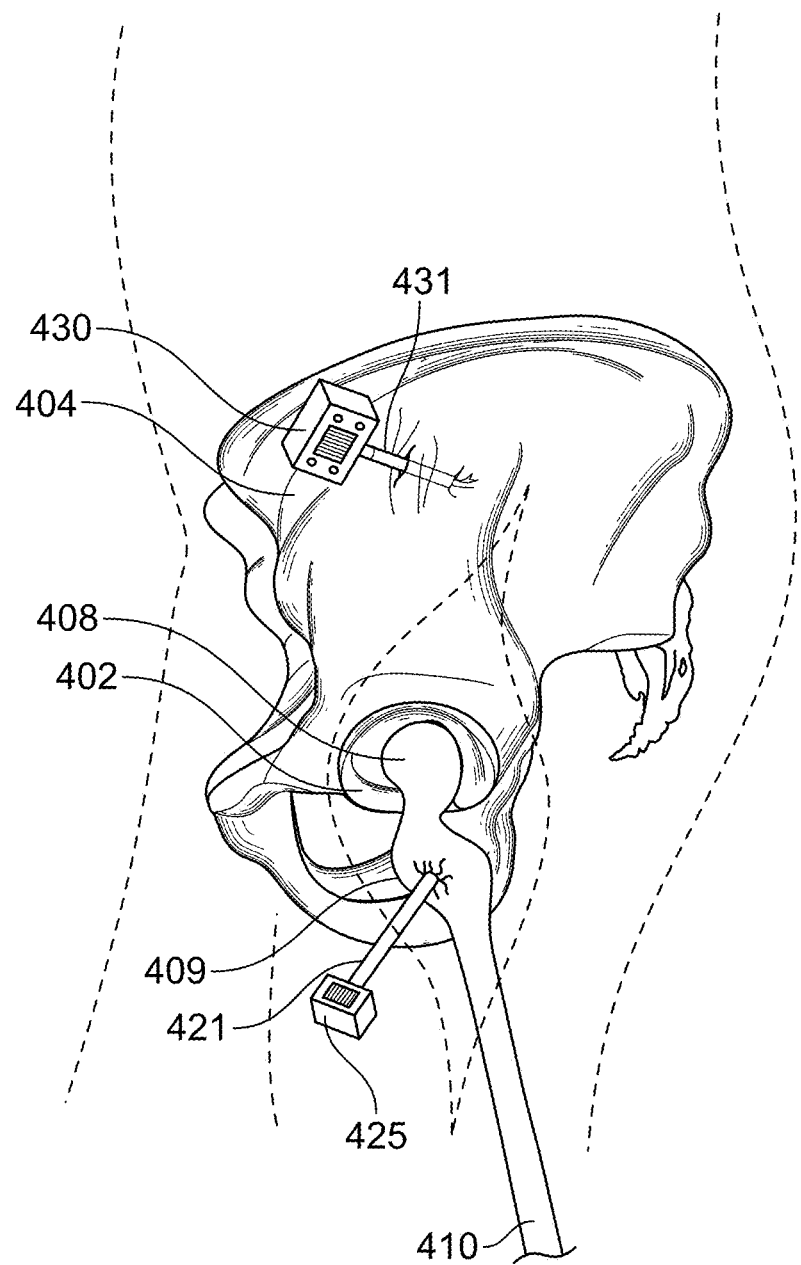
FIG. 4 is a pre-dislocation side view of a patient's pelvis, with a sensor unit attached thereto, and a femur having a sensor unit attached thereto.
Figure 5:
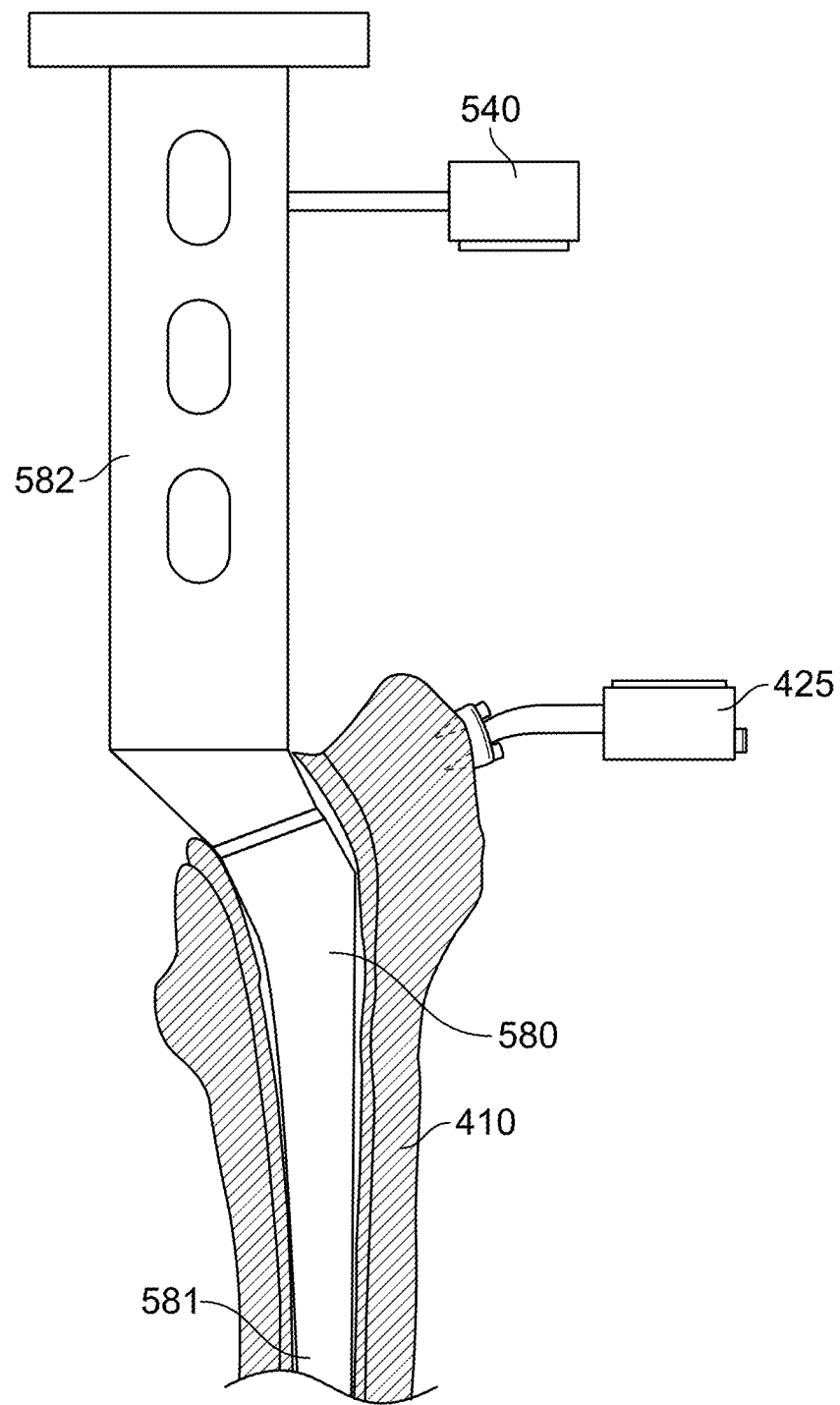
FIG. 5 is a cross-sectional view of a patient's femur, post-dislocation, having a broach inserted therein.
Figure 6:
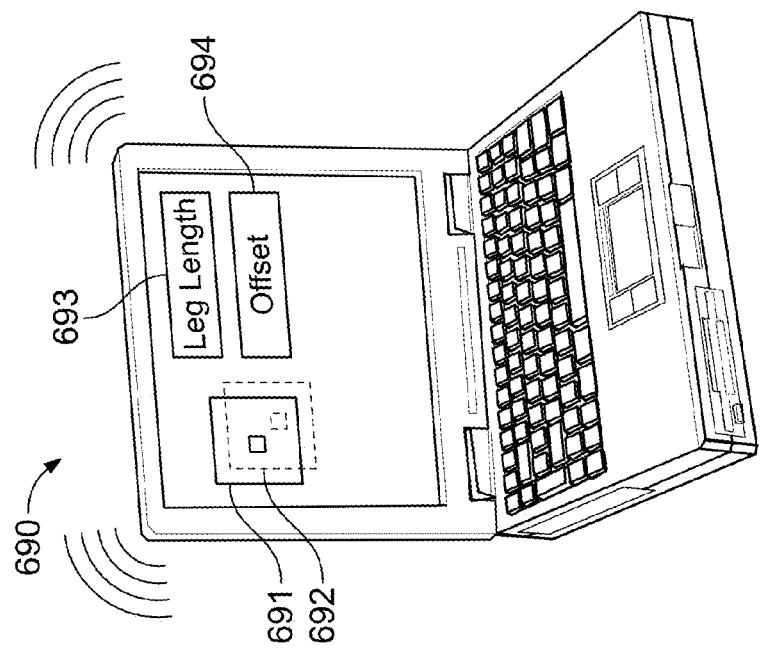
FIG. 6 is a side view of a patient's pelvis, having a sensor unit attached thereto, and a patient's femur having a sensor unit attached thereto, during a reduction procedure.
Figure 6:
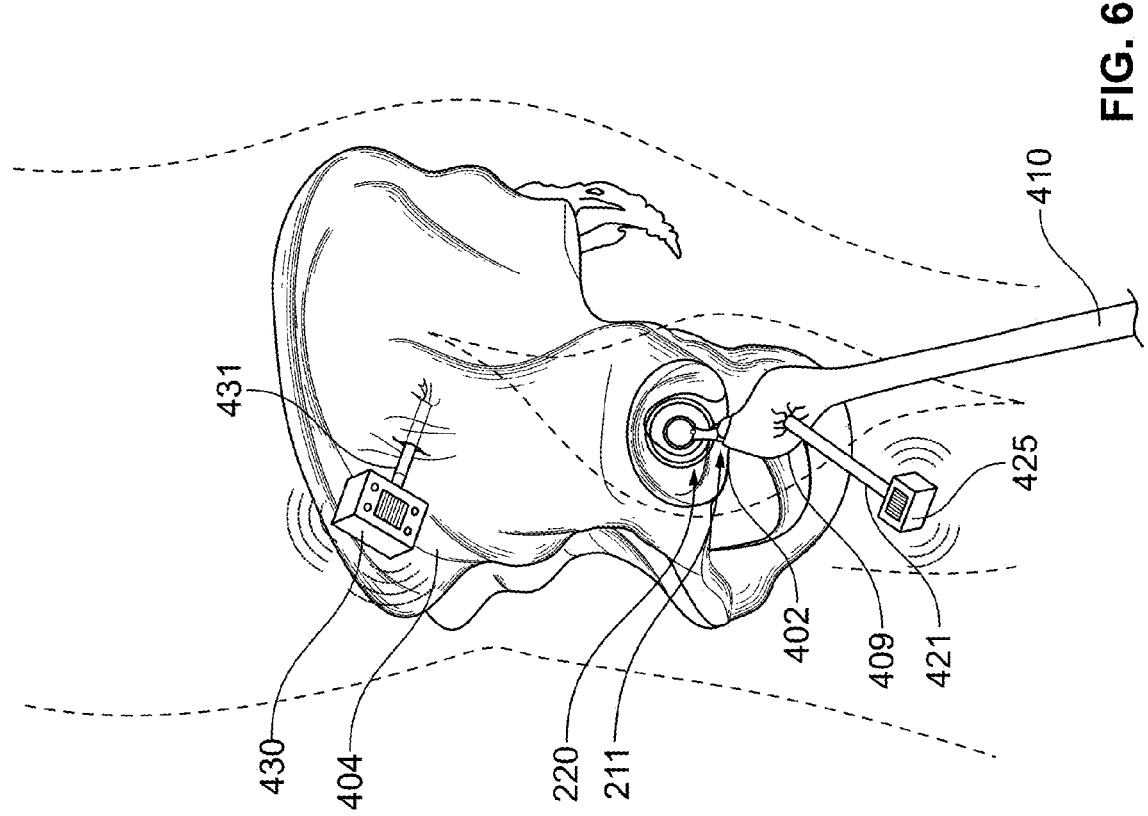

FIGS. 4-6 depict an exemplary embodiment of a hip replacement surgery employing the systems and methods disclosed herein. More specifically, FIG. 4 is a pre-dislocation side view of a patient's pelvis, with a sensor unit attached thereto, and a femur having a sensor unit attached thereto. FIG. 5 is a cross-sectional view of a patient's femur, post-dislocation, having a broach inserted therein, in order to perform a femoral registration. FIG. 6 is a side view of a patient's pelvis, having a sensor unit attached thereto, and a patient's femur having a sensor unit attached thereto, during a reduction procedure.

With reference to FIG. 4, a patient's pelvis 404 and femur 410 are illustrated. The surgical wound partly exposes the femur 410 and part of the greater trochanter 409. In order to measure the positional relationship between the femur 410 and the pelvis 404, a femur sensor unit 425 is coupled to the femur 410, and a pelvis sensor unit 430 is coupled to the pelvis 404. In one embodiment, the sensor unit 425 is coupled to the femur 410 using a pin or bone screw 421 proximate the greater trochanter 409. In another embodiment, the sensor unit 425 is positioned so that it lies along either the mechanical or anatomical femoral axis (e.g., it may be percutaneously coupled near the distal femur). Further, in one embodiment, the pelvis sensor unit 430 is coupled to the pelvis 404 using a pin or bone screw 431.

In operation, the sensor units 425, 430 measure the positional relationship between one another, which is then translated to the positional relationship between the femur 410 and the pelvis 404. More specifically, the sensor units 425, 430 measure up to 6-DOF between one another (e.g., roll, pitch, yaw, and three translational distances). The information measured by the femur sensor unit 425 and the pelvis 430 is transmitted to a computing device (e.g., computer 690 of FIG. 6), and contains enough information to determine the relative positioning of the sensor units, and therefore the relative positioning of the femur 410 with respect to the pelvis 404. This information, in conjunction with information regarding the femoral registration (discussed below), may be measured pre-dislocation, during a reduction procedure, and post-reduction. A comparison of the information measured pre-dislocation and post-reduction yields the actual changes in leg length and offset, as a result of the surgery. Similarly, the anterior-posterior change in femur position may be determined.

FIG. 5 is a cross-sectional view of a patient's femur 410, post-dislocation, having a broach 580 inserted therein. More specifically, FIG. 5 illustrates the use of a broach 580 to perform a femoral registration. The femoral registration may thereby define a femoral coordinate system.

In general, the coordinate system associated with the broach 580 consists of three axes, in which the dimensions of the broach can be described. For example, the three axes may include: one axis (e.g., x-axis), which points down the length of the broach; another axis (e.g., y-axis), which is perpendicular to the x-axis, and points along the offset dimension of the broach; and a third axis (e.g., z-axis), which perpendicular to both the x-axis and the y-axis. Likewise, in general, the coordinate system for the femur consists of three axes, in which the dimensions of the femur can be described. In one embodiment, the broach 580 may be positioned within the femur such that the coordinate system of the broach matches the coordinate system of the femur. In other words, the broach 580 may be positioned within the femur 410 such that the positional axes of the broach are collinear or otherwise parallel to the positional axes of the femur. The orientation between the broach 580 and the femur 410 may also be defined by three degrees of rotation. In one embodiment, the broach 580 is oriented to match the orientation of the femur 410.

A broach sensor unit 540 is coupled to the handle 582 of the broach 580. With the broach 580 thereby coupled to the femur 410, sensor unit 425 is activated to measure a positional relationship between the broach sensor unit 540 and the femur sensor unit 425. Such positional relationship, is used to register the femur 410. Registration of the femur 410 is used to relate the femur to a reference frame, which in this case is the femur sensor unit 425. In one embodiment, the femoral registration is performed by measuring 3-DOF of orientation (e.g., roll, pitch, and yaw) between the femur sensor unit 425 and the broach sensor unit 540. While FIG. 5 shows the broach 580 serving as an interface with the femur 410, the use of other more generic registration tools may be employed. Further, the coordinate system of the broach 580 preferably matches with a coordinate system of a femoral implant (i.e., the stem component 211, of FIG. 2, matches the broach stem 581). As such, the femoral registration with the broach can be translated to the femoral implant. In another embodiment, a modified femoral implant, which includes an implant sensor, can be used in place of the broach 580 to perform the femoral registration. In another embodiment, instead of using a dedicated broach sensor unit 540, the pelvis sensor unit 430 may be momentarily detached from the pelvis 404 and coupled to the broach 580 to perform the femoral registration.

FIG. 6 is a side view of a patient's pelvis 404, having a sensor unit 430 attached thereto, and the patient's femur 410 having a sensor unit 425 attached thereto, during a reduction procedure. FIG. 6 also shows a corresponding computer system 690 conveying a track frame 692, target frame 691, and leg length 693 and offset 694 changes. More specifically, FIG. 6 shows the artificial joint reduced (or assembled) after the implantation of the acetabular prosthetic 220 and the femoral prosthetic 211. The positional relationship between the femur sensor unit 425 and the pelvis sensor unit 430 can be measured, in real-time or proximate real-time, and transmitted wirelessly (or via wired communication) to computer system 690.

Figure 7A:
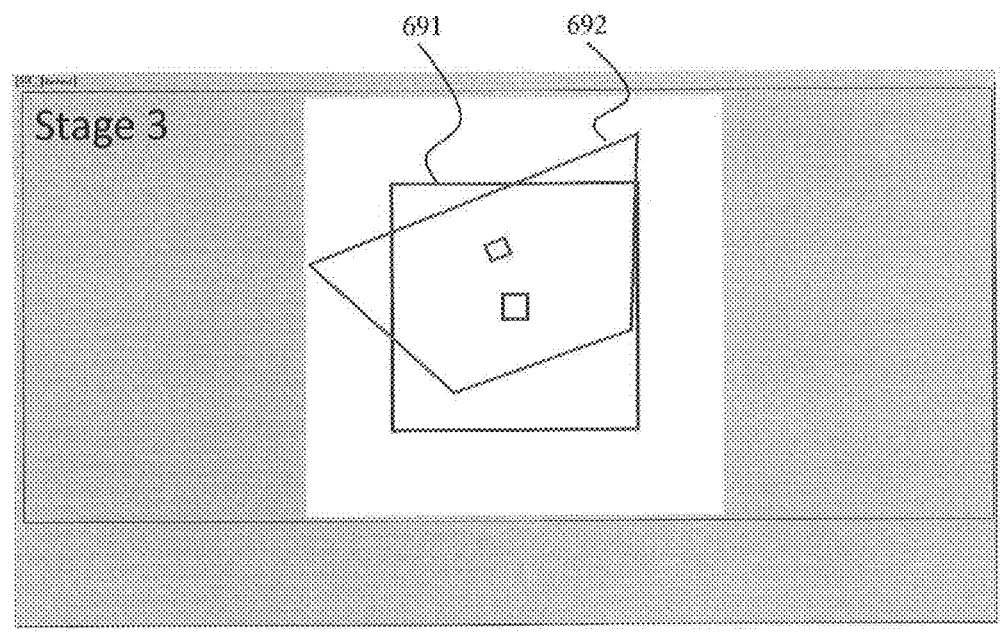
FIG. 7A is a screen shot of a track frame and respective target frame during a reduction procedure.
Figure 7B:
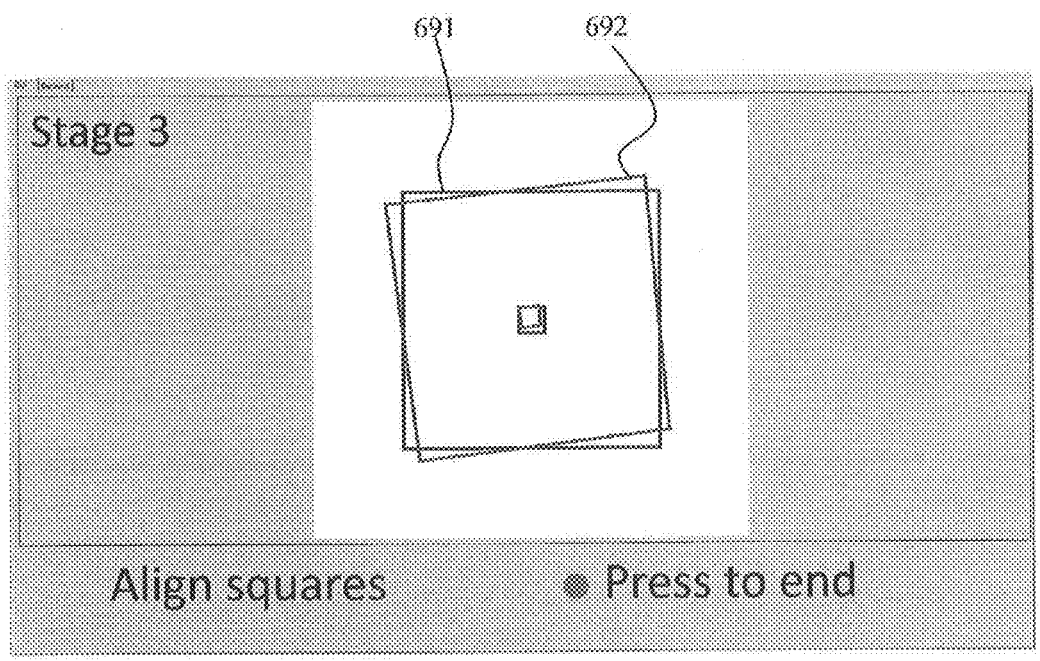
FIG. 7B is another screen shot a track frame and respective target frame during a reduction procedure.

A processor within computer system 690 uses the pre-dislocation positional relationship, femoral registration, and real-time positional relationship between the femur sensor unit and the pelvis sensor unit to display a target frame 691 and a tracking frame 692. In one embodiment, target frame 691 depicts the original orientation (e.g., the pre-dislocation measurements of the original roll, pitch, and yaw) between the femur 410 and the pelvis 404 (or between the femur sensor unit 425 and the pelvis sensor unit 430). FIG. 7A is a screen shot of a track frame 692 and respective target frame 691 during a reduction procedure. As shown in FIG. 7A, the track frame 692 is poorly aligned with the target frame 691. As such, the depiction indicates to a surgeon that the real-time orientation of the femur 410 does not coincide with the pre-dislocation orientation of the femur. FIG. 7B is another screen shot the track frame 692 and respective target frame 691, showing the track frame closely aligned with the target frame. Such depiction indicates to the surgeon that the reduction orientation of the femur 410 is approximating the pre-dislocation orientation of the femur.

Figure 7C:
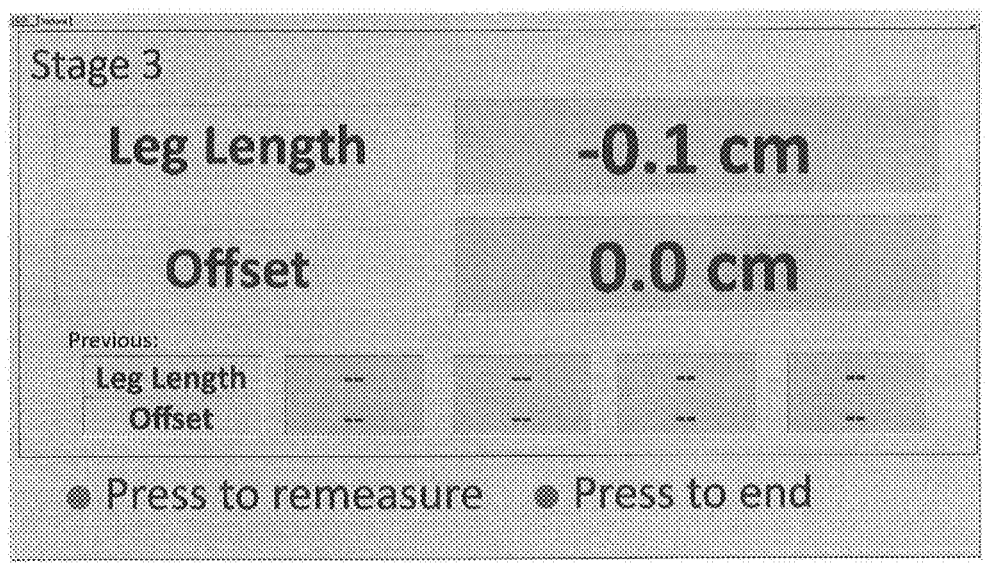
FIG. 7C is a screen shot displaying changes in leg length and offset after a reduction procedure.

In one embodiment, when the femur 410 is orientated to match the pre-dislocation orientation, both the track frame 692 and the target frame 691 are in complete alignment. The processor then calculates and conveys a post-reduction change in leg length and offset, as shown in FIG. 7C. In one embodiment, for example, when the femur 410 is orientated such that the track frame 692 matches the target frame 691, the processor: (1) measures up to three translational distances between the pelvis sensor unit 430 and the femur sensor unit 425; (2) calculates the differences between the pre-dislocation and post-reduction translational distances; and (3) displays the change in leg length and change in offset between the pelvis 404 and the femur 410 based on the calculated differences in distance and the reference frame obtained during the femoral registration. In other words, the processor converts or expresses differences in distance into the femoral coordinate system based on the femoral registration. While in the embodiment shown, the processor provides graphical and/or numerical displays, alternative embodiments include the use of any other audio/visual depiction or expression of the relevant information.

Additional Embodiments

In one embodiment, there is provided a system for performing a computer-assisted hip replacement surgery. The system includes: (1) a pelvis sensor unit configured to be coupled to a patient's pelvis; (2) a broach sensor unit configured to be coupled to a broach; (3) a femur sensor unit configured to be coupled to the patient's femur; and (4) a computer-readable storage medium having instructions executable, by at least one processing device, that when executed cause the processing device to perform functions that assist a physician during a hip replacement surgery. Specifically, the processor-executable instructions, when executed prior to a dislocation of the femur from the pelvis, wherein the pelvis sensor unit is coupled to the pelvis and the femur sensor unit is coupled to the femur, cause the processing device to measure a pre-dislocation positional relationship between the pelvis sensor unit and the femur sensor unit. Further, when executed after the dislocation of the femur from the pelvis, wherein the broach sensor unit is coupled to the broach, the femur sensor unit is coupled to the femur, and the broach is inserted within the femur, cause the processing device to perform a femoral registration by measuring an orientation between the broach sensor unit and the femur sensor unit. Additionally, when executed during a reduction procedure, wherein the pelvis sensor unit is coupled to the pelvis and the femur sensor unit is coupled to the femur, cause the processing device to display a fixed target frame and a track frame, wherein the track frame depicts a reduction orientation between the femur sensor unit and the pelvis sensor unit. Finally, when executed after the femur has been positioned such that the track frame matches the target frame, cause the processing device to (1) measure a post-reduction translational distance between the pelvis sensor unit and the femur sensor unit and (2) calculate and display a change in leg length and a change in offset based the pre-dislocation positional relationship and the femoral registration.

The computer-readable storage medium may further includes instructions, which when executed, cause the processing device to calculate and display a change in anterior-posterior femur position based the pre-dislocation positional relationship and the femoral registration.

The pre-dislocation positional relationship may include a translational component and an orientation component. As such, the fixed target frame may depict the pre-dislocation orientation. Alternatively, the pre-dislocation positional relationship may be defined by roll, pitch, yaw, and three perpendicular translational distances between the pelvis sensor unit relative to the femur sensor unit. As such, the fixed target frame may depict the pre-dislocation roll, pitch, and yaw.

The femoral registration may thereby define a femoral coordinate system. In one embodiment, a coordinate system of the broach matches a coordinate system of the femur, such that the broach coordinate system is used to define the femoral coordinate. The orientation between the broach sensor unit and the femur sensor unit may be defined by three degrees of rotation. Additionally, the broach may be aligned and positioned within the femur such that the positional axes of the broach are collinear or parallel to the positional axes of the femur. As would be understood by one of skill in the art, the femoral coordinate system may be defined in multiple ways, and alternative embodiments may call for alternative definitions of the femoral coordinate system.

In one embodiment, the femur sensor unit includes an optical reader, and the pelvis sensor unit and the broach sensor unit include a beacon. Alternatively, the pelvis sensor unit and the broach sensor unit may include an optical reader, and the femur sensor unit may include a beacon.

In another embodiment, there is provided a system for performing hip replacement surgery, comprising: (a) means for measuring a pre-dislocation positional relationship between a patient's pelvis and the patient's femur; (b) means for performing a registration of the femur; (c) means for tracking the position of the femur, with respect to the pelvis, during a reduction procedure; (d) means for displaying the position of the femur, relative to the pelvis, during the reduction procedure; (e) means for calculating change in leg length, offset, and/or anterior-posterior position of the femur post-reduction; and/or (f) means for conveying the change in leg length, offset, and/or anterior-posterior position of the femur post-reduction.

In yet another embodiment, there is provided a method for performing a hip replacement surgery, comprising: (a) measuring a pre-dislocation positional relationship between a femur sensor unit coupled to the patient's femur and a pelvis sensor unit coupled to the patient's pelvis; (b) performing a post-dislocation femoral registration by measuring an orientation between the femur sensor unit and a broach sensor unit coupled to a broach inserted within the patient's femur; (c) measuring an orientation between the femur sensor unit and the pelvis sensor unit during a reduction procedure; and (d) calculating a change in leg length and a change in offset, based on the pre-dislocation positional relationship and the femoral registration. The method may further include (e) conveying the change in leg length and the change in offset.

In another embodiment, there is provided a method for performing a hip replacement surgery, comprising: (a) measuring a pre-dislocation translational position and orientation between a pelvis sensor unit coupled to a patient's pelvis and a femur sensor unit coupled to the patient's femur; (b) registering the femur after the femur has been dislocated from the pelvis; (c) displaying a graphic mapping the pre-dislocation orientation against a real-time orientation between the pelvis sensor unit and the femur sensor unit, during a reduction procedure; and (d) calculating a change in leg length and a change in offset, after the reduction procedure, based on the pre-dislocation translational position and the registration of the femur. The method may further include (e) conveying the change in leg length and the change in offset. The femur may be registered by measuring an orientation between the femur sensor unit and a registration sensor unit coupled to a registration tool. The femur may alternatively be registered by measuring an orientation between the femur sensor unit and a broach sensor unit coupled to a broach inserted within the patient's femur.

In still another embodiment, there is provided a method or performing a hip replacement surgery, comprising: (a) measuring a pre-dislocation leg length and offset between a patient's pelvis and the patient's femur; (b) registering the femur after the femur has been dislocated from the pelvis; (c) tracking the position of the femur relative to the pelvis during a reduction procedure; and (d) calculating a change in leg length and a change in offset, after the reduction procedure, based on the registration of the femur and the pre-dislocation leg length and offset measurement. The method may further include (e) conveying the change in leg length and the change in offset. The femur may be registered by measuring an orientation between the femur and a registration tool.

Communication Between Components of the Present Invention.

In one embodiment, data communication between the system components of the present invention is accomplished over a network consisting of electronic devices connected either physically or wirelessly, wherein data is transmitted from one device to another. Such devices (e.g., end-user devices) may include, but are not limited to: a desktop computer, a laptop computer, a handheld device or PDA, a cellular telephone, a set top box, an television system, a mobile device or tablet, or systems equivalent thereto. Exemplary networks include a Local Area Network, a Wide Area Network, an organizational intranet, the Internet, or networks equivalent thereto. The functionality and system components of an exemplary computer and network are further explained in conjunction with FIG. 8, below.

Computer Implementation.

Figure 8:
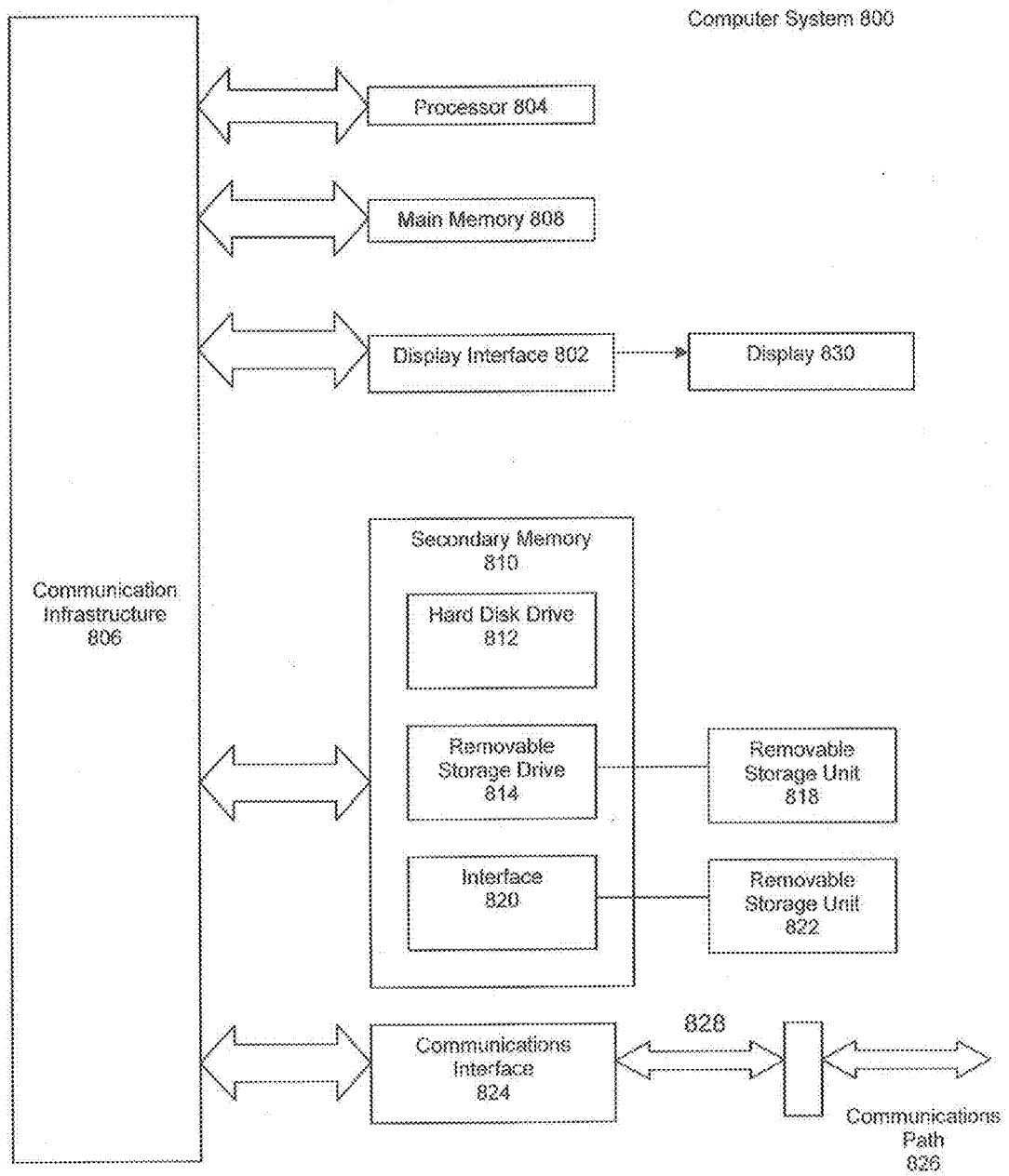
FIG. 8 is a schematic drawing of a computer system used to implement the methods presented.

In one embodiment, the invention is directed toward one or more computer systems capable of carrying out the functionality described herein. For example, FIG. 8 is a schematic drawing of a computer system 800 used to implement the methods presented above. Computer system 800 includes one or more processors, such as processor 804. The processor 804 is connected to a communication infrastructure 806 (e.g., a communications bus, cross-over bar, or network). Computer system 800 can include a display interface 802 that forwards graphics, text, and other data from the communication infrastructure 806 (or from a frame buffer not shown) for display on a local or remote display unit 830.

Computer system 800 also includes a main memory 808, such as random access memory (RAM), and may also include a secondary memory 810. The secondary memory 810 may include, for example, a hard disk drive 812 and/or a removable storage drive 814, representing a floppy disk drive, a magnetic tape drive, an optical disk drive, flash memory device, etc. The removable storage drive 814 reads from and/or writes to a removable storage unit 818. Removable storage unit 818 represents a floppy disk, magnetic tape, optical disk, flash memory device, etc., which is read by and written to by removable storage drive 814. As will be appreciated, the removable storage unit 818 includes a computer usable storage medium having stored therein computer software, instructions, and/or data.

In alternative embodiments, secondary memory 810 may include other similar devices for allowing computer programs or other instructions to be loaded into computer system 800. Such devices may include, for example, a removable storage unit 822 and an interface 820. Examples of such may include a program cartridge and cartridge interface (such as that found in video game devices), a removable memory chip (such as an erasable programmable read only memory (EPROM), or programmable read only memory (PROM)) and associated socket, and other removable storage units 822 and interfaces 820, which allow computer software, instructions, and/or data to be transferred from the removable storage unit 822 to computer system 800.

Computer system 800 may also include a communications interface 824. Communications interface 824 allows computer software, instructions, and/or data to be transferred between computer system 800 and external devices. Examples of communications interface 824 may include a modem, a network interface (such as an Ethernet card), a communications port, a Personal Computer Memory Card International Association (PCMCIA) slot and card, etc. Software and data transferred via communications interface 824 are in the form of signals 828 which may be electronic, electromagnetic, optical or other signals capable of being received by communications interface 824. These signals 828 are provided to communications interface 824 via a communications path (e.g., channel) 826. This channel 826 carries signals 828 and may be implemented using wire or cable, fiber optics, a telephone line, a cellular link, a radio frequency (RF) link, a wireless communication link, and other communications channels.

In this document, the terms "computer-readable storage medium," "computer program medium," and "computer usable medium" are used to generally refer to media such as removable storage drive 814, removable storage units 818, 822, data transmitted via communications interface 824, and/or a hard disk installed in hard disk drive 812. These computer program products provide computer software, instructions, and/or data to computer system 800. These computer program products also serve to transform a general purpose computer into a special purpose computer programmed to perform particular functions, pursuant to instructions from the computer program products/software. Embodiments of the present invention are directed to such computer program products.

Computer programs (also referred to as computer control logic) are stored in main memory 808 and/or secondary memory 810. Computer programs may also be received via communications interface 824. Such computer programs, when executed, enable the computer system 800 to perform the features of the present invention, as discussed herein. In particular, the computer programs, when executed, enable the processor 804 to perform the features of the presented methods. Accordingly, such computer programs represent controllers of the computer system 800. Where appropriate, the processor 804, associated components, and equivalent systems and sub-systems thus serve as "means for" performing selected operations and functions. Such "means for" performing selected operations and functions also serve to transform a general purpose computer into a special purpose computer programmed to perform said selected operations and functions.

In an embodiment where the invention is implemented using software, the software may be stored in a computer program product and loaded into computer system 800 using removable storage drive 814, interface 820, hard drive 812, communications interface 824, or equivalents thereof. The control logic (software), when executed by the processor 804, causes the processor 804 to perform the functions and methods described herein.

In another embodiment, the methods are implemented primarily in hardware using, for example, hardware components such as application specific integrated circuits (ASICs). Implementation of the hardware state machine so as to perform the functions and methods described herein will be apparent to persons skilled in the relevant art(s). In yet another embodiment, the methods are implemented using a combination of both hardware and software.

Embodiments of the invention, including any systems and methods described herein, may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing firmware, software, routines, instructions, etc.

For example, in one embodiment, there is provided a computer-readable storage medium for performing a hip replacement surgery, comprising instructions executable by at least one processing device that, when executed, cause the processing device to: (a) measure a pre-dislocation positional relationship between a femur sensor unit coupled to the patient's femur and a pelvis sensor unit coupled to the patient's pelvis; (b) perform a post-dislocation femoral registration by measuring an orientation between the femur sensor unit and a broach sensor unit coupled to a broach inserted within the patient's femur; (c) measure an orientation between the femur sensor unit and the pelvis sensor unit during a reduction procedure, and (d) calculate a change in leg length and a change in offset, based on the pre-dislocation positional relationship and the femoral registration. The computer-readable storage medium may, further comprise instructions executable by at least one processing device that, when executed, cause the processing device to (e) convey the change in leg length and the change in offset.

In another embodiment, there is provided a computer-readable storage medium for performing a hip replacement surgery, comprising instructions executable by at least one processing device that, when executed, cause the processing device to: (a) measure a pre-dislocation translational position and orientation between a pelvis sensor unit coupled to a patient's pelvis and a femur sensor unit coupled to the patient's femur; (b) register the femur after the femur has been dislocated from the pelvis; (c) display a graphic mapping the pre-dislocation orientation against a real-time orientation between the pelvis sensor unit and the femur sensor unit, during a reduction procedure; and (d) calculate a change in leg length and a change in offset, after the reduction procedure, based on the pre-dislocation translational position and the registration of the femur. The computer-readable storage medium may further comprise instructions executable by at least one processing device that, when executed, cause the processing device to (e) convey the change in leg length and the change in offset.

In still another embodiment, there is provided a computer-readable storage medium for performing a hip replacement surgery, comprising instructions executable by at least one processing device that, when executed, cause the processing device to: (a) measure a pre-dislocation leg length and offset between a patient's pelvis and the patient's femur; (b) register the femur after the femur has been dislocated from the pelvis; (c) track the position of the femur relative to the pelvis during a reduction procedure; and (d) calculate a change in leg length and a change in offset, after the reduction procedure, based on the registration of the femur and the pre-dislocation leg length and offset measurement. The computer-readable storage medium may further comprise instructions executable by at least one processing device that, when executed, cause the processing device to (e) convey the change in leg length and the change in offset.

CONCLUSION

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent structures, components, methods, and means.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. Further, each system component and/or method step presented should be considered a "means for" or "step for" performing the function described for said system component and/or method step. As such, any claim language directed to a "means for" or "step for" performing a recited function refers to the system component and/or method step in the specification that performs the recited function, as well as equivalents thereof.

It is to be appreciated that the Detailed Description section, and not the Summary and Abstract sections, is intended to be used to interpret the claims. The Summary and Abstract sections may set forth one or more, but not all exemplary embodiments of the present invention as contemplated by the inventor(s), and thus, are not intended to limit the present invention and the appended claims in any way.

What is claimed is:

1. A system for performing a computer-assisted hip replacement surgery, comprising:
    a pelvis sensor unit configured to be coupled to a patient's pelvis;
    a broach sensor unit configured to be coupled to a broach;
    a femur sensor unit configured to be coupled to the patient's femur; and
    a computer-readable storage medium having instructions executable, by at least one processing device,
    (a) which when executed prior to a dislocation of the femur from the pelvis, wherein the pelvis sensor unit is coupled to the pelvis and the femur sensor unit is coupled to the femur, cause the processing device to measure a pre-dislocation positional relationship between the pelvis sensor unit and the femur sensor unit to define a fixed target frame,
    (b) and which when executed after the dislocation of the femur from the pelvis, wherein the broach sensor unit is coupled to the broach, the femur sensor unit is coupled to the femur, and the broach is inserted within the femur such that positional axes of the broach are collinear or parallel to positional axes of the femur and the coordinate system of the broach matches the coordinate system of the femur, cause the processing device to perform an anatomical registration of the femur to define a femoral coordinate system by measuring, in a single registration measurement, an orientation in three degrees of freedom between the broach sensor unit and the femur sensor unit,
    (c) and which when executed during a reduction procedure, wherein the pelvis sensor unit is coupled to the pelvis and the femur sensor unit is coupled to the femur, cause the processing device to display the fixed target frame and a track frame, wherein the track frame depicts a reduction orientation between the femur sensor unit and the pelvis sensor unit, and
    (d) and which when executed after the femur has been positioned such that the track frame matches the target frame, cause the processing device to (1) measure a post-reduction translational distance between the pelvis sensor unit and the femur sensor unit and (2) calculate and display in the femoral coordinate system a change in leg length and a change in offset based on the post-reduction translational distance and the pre-dislocation positional relationship.

2. The system of claim 1, wherein the instructions configure the processing device to measure up to three post-reduction distances between the pelvis sensor unit and the femur sensor unit, calculate differences between the post-reduction translational distances and respective pre-dislocation translational distances and display the change in leg length and change in offset between the pelvis and the femur based on the calculated differences in distance in the femoral coordinate system obtained during the anatomical registration of the femur.

3. The system of claim 1, wherein the femur sensor unit includes an optical reader, and the pelvis sensor unit and the broach sensor unit include a beacon.

4. The system of claim 1, wherein the pelvis sensor unit and the broach sensor unit include an optical reader, and the femur sensor unit includes a beacon.

5. The system of claim 1, wherein the pre-dislocation positional relationship includes a translational component and an orientation component.

6. The system of claim 5, wherein the fixed target frame depicts the pre-dislocation orientation.

7. The system of claim 1, wherein the fixed target frame depicts the pre-dislocation roll, pitch, and yaw.

8. The system of claim 1, wherein the computer-readable storage medium further includes instructions, which when executed, cause the processing device to calculate and display a change in anterior-posterior femur position based on the pre-dislocation positional relationship and the anatomical registration of the femur.

9. A computer-readable storage medium for performing a hip replacement surgery, comprising:
    instructions executable by at least one processing device that, when executed, cause the processing device to
    (a) measure a pre-dislocation positional relationship between a femur sensor unit coupled to the patient's femur and a pelvis sensor unit coupled to the patient's pelvis,
    (b) perform a post-dislocation anatomical registration of the femur to define a femoral coordinate system by measuring, in a single registration measurement, an orientation in three degrees of freedom between the femur sensor unit and a broach sensor unit coupled to a broach inserted within the patient's femur such that positional axes of the broach are collinear or parallel to positional axes of the femur and the coordinate system of the broach matches the coordinate system of the femur,
    (c) measure a reduction orientation between the femur sensor unit and the pelvis sensor unit during a reduction procedure, and
    (d) calculate a change in leg length and a change in offset, based on the pre-dislocation positional relationship, the reduction orientation and the anatomical registration of the femur.

10. The computer-readable storage medium of claim 9, further comprising:
    instructions executable by at least one processing device that, when executed, cause the processing device to
    (e) display in the femoral coordinate system the change in leg length and the change in offset.

11. A computer-readable storage medium for performing a hip replacement surgery, comprising:
    instructions executable by at least one processing device that, when executed, cause the processing device to
    (a) measure a pre-dislocation translational position and orientation between a pelvis sensor unit coupled to a patient's pelvis and a femur sensor unit coupled to the patient's femur,
    (b) perform an anatomical registration of the femur to define a femoral coordinate system by measuring, in a single registration measurement, an orientation in three degrees of freedom between a femur sensor unit coupled to the femur and a broach sensor unit coupled to a broach inserted within the patient's femur after the femur has been dislocated from the pelvis such that positional axes of the broach are collinear or parallel to positional axes of the femur and the coordinate system of the broach matches the coordinate system of the femur, (c) display a graphic mapping the pre-dislocation orientation against a real-time orientation between the pelvis sensor unit and the femur sensor unit, during a reduction procedure, and (d) calculate a change in leg length and a change in offset, after the reduction procedure, based on the pre-dislocation translational position, a post-reduction translational distance between the femur sensor unit and pelvis sensor unit and the femoral coordinate system.

12. The computer-readable storage medium of claim 11, further comprising:

instructions executable by at least one processing device that, when executed, cause the processing device to (e) display in the femoral coordinate system the change in leg length and the change in offset.

13. A computer-readable storage medium for performing a hip replacement surgery, comprising:

instructions executable by at least one processing device that, when executed, cause the processing device to (a) measure a pre-dislocation leg length and offset between a patient's pelvis and a patient's femur using data obtained from any one of (1) a preoperative scan of the patient's pelvis and the patient's femur and (2) respective sensor units coupled to the patient's pelvis and the patient's femur, (b) perform an anatomical registration of the femur to define a femoral coordinate system by measuring, in a single registration measurement, an orientation in three degrees of freedom between a femur sensor unit coupled to the femur and a broach sensor unit coupled to a broach inserted within the patient's femur after the femur has been dislocated from the pelvis such that positional axes of the broach are collinear or parallel to positional axes of the femur and a coordinate system of the broach matches a coordinate system of the femur, (c) track a position of the femur relative to the pelvis during a reduction procedure, and (d) calculate a change in leg length and a change in offset, after the reduction procedure, based on the femoral coordinate system and the pre-dislocation leg length and offset measurement.

14. The computer-readable storage medium of claim 13, further comprising:

instructions executable by at least one processing device that, when executed, cause the processing device to (e) display in the femoral coordinate system the change in leg length and the change in offset.

15. The system of claim 1 wherein the pelvis sensor unit and the broach sensor unit comprise a single selectively detachable sensor unit configured to individually and detachably couple to the pelvis and the broach.

16. The computer-readable storage medium of claim 9 wherein the pelvis sensor unit and the broach sensor unit comprise a single selectively detachable sensor unit configured to individually and detachably couple to the pelvis and the broach.

17. The computer-readable storage medium of claim 11 wherein the pelvis sensor unit and the broach sensor unit comprise a single selectively detachable sensor unit configured to individually and detachably couple to the pelvis and the broach.

18. The computer-readable storage medium of claim 13, wherein the broach sensor unit comprises a selectively detachable sensor unit and wherein the instructions executable by at least one processing device that, when executed, cause the processing device to measure the pre-dislocation leg length and offset using the selectively detachable sensor when coupled to the pelvis and track the position of the femur relative to the pelvis when the selectively detachable sensor unit is re-coupled to the pelvis.

* * * * *